US00PP08787P

United States Patent [19]

Heidgen

[11] Patent Number: Plant 8,787

[45] Date of Patent: Jun. 14, 1994

[54] GERANIUM, SOLO

[76] Inventor: Charles F. Heidgen, 821 Walnut St., Batavia, Ill. 60510

[21] Appl. No.: 120,548

[22] Filed: Sep. 14, 1993

[51] Int. Cl.[5] ..... A01H 5/00

[52] U.S. Cl. ..... Plt./87.12

[58] Field of Search ..... Plt. 87.12

*Primary Examiner*—James R. Feyrer

[57] ABSTRACT

An F3 hybrid geranium plant named 'Solo', from an initial cross of 'Nicor Star'×'Tang', characterized particularly by its compact but freely branching habit; dark brown zoned, deep green, attractive and unusually dense foliage; and, prolific presentation of attractive umbels. Individual flowers are single, having five petals, and are uniquely large and individually discernable due to the predominant pale pink petal color which contrasts with the deep pink coloration of petal bases and basal margin portions which give each flower a conspicuous eye.

1 Drawing Sheet

BACKGROUND OF THE INVENTION

The present invention, hereinafter referred to by the cultivar name "Solo" relates to a new and distinct geranium. "Solo" is a new and improved plant resulting from a planned breeding program as performed by me in my greenhouse at 821 Walnut Street, Batavia, Ill. My breeding program began in March 1977, and has been ongoing since that time. This seedling was originally identified in my records by 87 S 010 and was an f3 seedling of Nicor Star, an unpatented Dwarf geranium that resulted from a cross between Tang (the seed parent), an unpatented Dwarf geranium and Red Star (the pollen parent), an unpatented Zonal geranium. Being a cross between two market class zonal geranium plants, it is believed that the botanical classification *Pelargonium×hortorum* would be appropriate for this plant.

Upon recognition of the outstanding characteristics of this plant, it was selected from the progeny of the stated cross, and was set aside for further observation and testing and was subsequently named "Solo." Asexual reproduction of "Solo" has been repeatedly accomplished by the rooting of vegetative cuttings in my greenhouse in Batavia, Ill. Examination of the plants so propagated through a series of propagations has demonstrated that the combination of characteristics herein disclosed for "Solo" are firmly fixed and retained through successive generations through asexual reproduction.

SUMMARY OF THE INVENTION

The new and distinguishing characteristics of "Solo" reside primarily in its compact growth habit, its prolific blooming characteristic and its medium-sized, dark green foliage with definite zonation. This geranium also has medium to large single flowers with a unique pale pink color and darker pink eye and edges, as well as high heat tolerance. This plant might be seen as a novel and desirable introduction within the industry by a combination of desired traits including:

Being particularly adapted to culture in the ground or in pots due to its compact growth habit, dense leafy canopy and its tendency to branch prolifically. Forming a bushy plant mass in approximately 7–9 weeks from one plantlet, and a plant that is not stretched or leggy, but rather dense.

Having a generous amount of foliage, with dark green coloration and conspicuous zonation over the medium sized leaves and of higher than normal density.

Presenting an unusually high number of well filled umbels of varied states of maturity placed well above the foliage mass, and having a unique pale pink floret coloration, with a darker pink center and edges, which is distinctively, contrastingly highlighted over and against the dark green foliage.

Having a large number of umbels with a generous number of open, single petal florets of medium to large size and appearance, borne on pedicels which present the florets in a loose arrangement to form umbels having a somewhat open, globular shape.

Presenting a large number of umbels which also vary in stage of maturity, which gives the plant an attractive appearance for an extended period of time, rather than being one that blooms in discontinuous flushes.

The color definitions to follow have been taken from *The Royal Horticultural Colour Chart* of The Royal Horticultural Society, London, where presented by the letters RHS followed by a color grouping indication, the number indicating the color patch and the letter indicating the shade, except where color definitions in general terms of ordinary meaning are presented. Plant descriptions were made from specimens grown under greenhouse conditions during daylight hours in Batavia, Ill.

BRIEF DESCRIPTION OF THE DRAWING

The photograph depicts a market unit made up of four market stage specimens of the plant growing in a 12" pot, in a stage of inflorescence. The assemblage is shown in an upper side view, depicting the characteristics of branching, leaves, leaf coloration and zonation, the number and varied stages of buds and flowers, and the positioning of the flower heads relative to the mass of the plants in the pot.

BOTANICAL DESCRIPTION OF THE PLANT

Botanical classification: *Pelargonium ×hortorum.*

Market class: Zonal Geranium suitable for planting in the ground or in containers.

Market name: "Solor".

Growth: "Solo" is a prolific blooming Geranium with single flowers and the truss or flower head is of medium size. The growth is upright in habit and given to branching freely.

Growth rate: Average, producing a typical 4½" flowering geranium in about 7 to 9 weeks from one 2¼" plantlet using standard commercial culture. Blooming habit: Exceptionally profuse and continuously blooming plant throughout the year, outdoors during the frost-free period, or in the greenhouse; a mature 4½" pot commonly producing a range of 4 to 7 flower heads at one time, in varying states of maturity.

INFLORESCENCE Flower heads:

*Size.*—3¼ to 3¾ inches across when the florets are fully open.

*Count.*—4 to 7 present at one time.

Truss:

*Size.*—Medium to large size; ranges from 3¼ to 3¾ inches in diameter.

*Shape.*—Rather loose, a flattened globe as it opens.

*Number of florets.*—Variable, range from approximately 13 to 29, average 18 to 22.

*Lasting quality.*—Average. Blooms last 4 to 8 days, possibly longer in cooler, dry weather.

Buds:

*Sepals.*—Shape — Long, above average width, pointed. Color — RHS Greyed Red Group, 178 A.

*Color.*—RHS Yellow Group, 4D.

*Form.*—Long and somewhat thick, slight point.

Florets:

*Number.*—18 to 28.

*Form.*—Rather cupped to flat, as it opens fully.

*Size.*—Ranging from ⅞ inch to 1½ inches across a fully open floret.

Petals:

*Number.*—Five.

*Size.*—Ranging from about 9/16 to 15/16 inches long and approximately 3/8 to 11/16 inches across.

*Texture.*—Soft.

*Appearance.*—Bright.

*Color.*—RHS Red Group, 56 D main part of the petal with a RHS Red Group 55 A center and extremely narrow edge.

Petaloids:

*Number.*—Substantially absent but may occur in numbers of up to five.

*Shape.*—Variable, often misshapen.

*Color.*—Very similar to that of the petals.

*Size.*—3/16 to 5/16 inches long and ⅝ to ⅞ inches long.

Sepals:

*Number.*—Usually 5.

*Color.*—RHS Greyed Red Group, 178 A.

Pedicel:

*Length.*—About ⅞ to 1 3/16 inches long.

*Color.*—RHS Greyed Purple Group, 184 A.

Peduncle:

*Arises.*—From node, opposed to leaf petiole.

*Pubescence.*—Normal.

*Color.*—RHS Yellow Green Group, 146 A.

REPRODUCTIVE ORGANS

Androecium:

*Stamens.*—Number — 5 to 7. Shape — Ribbon-like filaments jointed at bases. Color — Rose purple. Anther Attachment — versatile.

Anthers.—Number — 5 to 7. Shape — Normal, well developed. Color — Purple.

Gynoecium:

*Pistil.*—Number — One, compound. Length — Within the range of 3/32 to 5/32 inches.

*Stigma.*—Color — Purple.

*Style.*—Color — Green.

*Ovary.*—Size — Approximately 1/32 to 1/16 inches long.

Fertility: Normal, viable seed is produced.

Behavior: Once the plant beings to bloom, it has an exceptionally prolific blooming habit and yields a striking display of medium to large sized, single flowers of pale pink color with a darker, rose pink center and edging on the petals against its medium sized, dark green leaves with foliage.

General observations: Inflorescence is of medium to large size and of rather open heads which are an attractive contrast to the dark green, zoned foliage of the plant, and measure up to about 3 inches in diameter. At optimum stage of opening, florets are distinctive and striking with their pale pink coloration and darker, rose pink center and edges. Flowers have high heat tolerance when compared to other varieties.

STEM

Thickness: Medium.

Internodes: Short to very short under full light conditions.

Branching: Very free breaking.

Attitude: Upright, bushy habit.

FOLIAGE

Leaves:

*Quantity.*—Abundant.

*Shape.*—Reniform.

*Size.*—Medium, largest leaves range from about 2½ to 2⅞ inches across.

*Margin.*—Crenate.

*Texture.*—Somewhat pubescent, matt texture.

*Coloration.*—Dark green, RHS Green Group, 139 A, with a medium-sized zone of RHS Brown Group, 200 D. Zonation is centrally located on the leaf surface, and concentric to the point of the petiole attachment and with green surface portions both inside and outside the zonal band.

Petioles:

*Texture.*—Lightly pubescent.

*Length.*—Approximately 1⅞ to 2⅝ inches.

*Color.*—RHS Yellow Green Group, 146C.

"Solor" is comparable to "Rio" with which it shares market class, but is easily distinguishable therefrom in terms of flower color; "Solo" having pale pink petal coloration with a darker, rose pink eye in the center of each floret, as well as a darker, rose pink edge on each petal, while the petals of "Rio" are darker pink with magenta markings, not forming an eye. "Solo" is readily distinguished from "Fox" by having florets of much lighter petal coloration and bi-color effect, in addition to a much darker leaf coloration and a bolder, darker leaf zonation.

I claim:

1. A new and distinct variety of Geranium plant, substantially as shown and described, characterized by its upright, bushy growth habit; its medium-sized dark green foliage with zonation; its pale pink flowers with darker, rose pink center and edges; its abundant blooming habit and its heat tolerance.

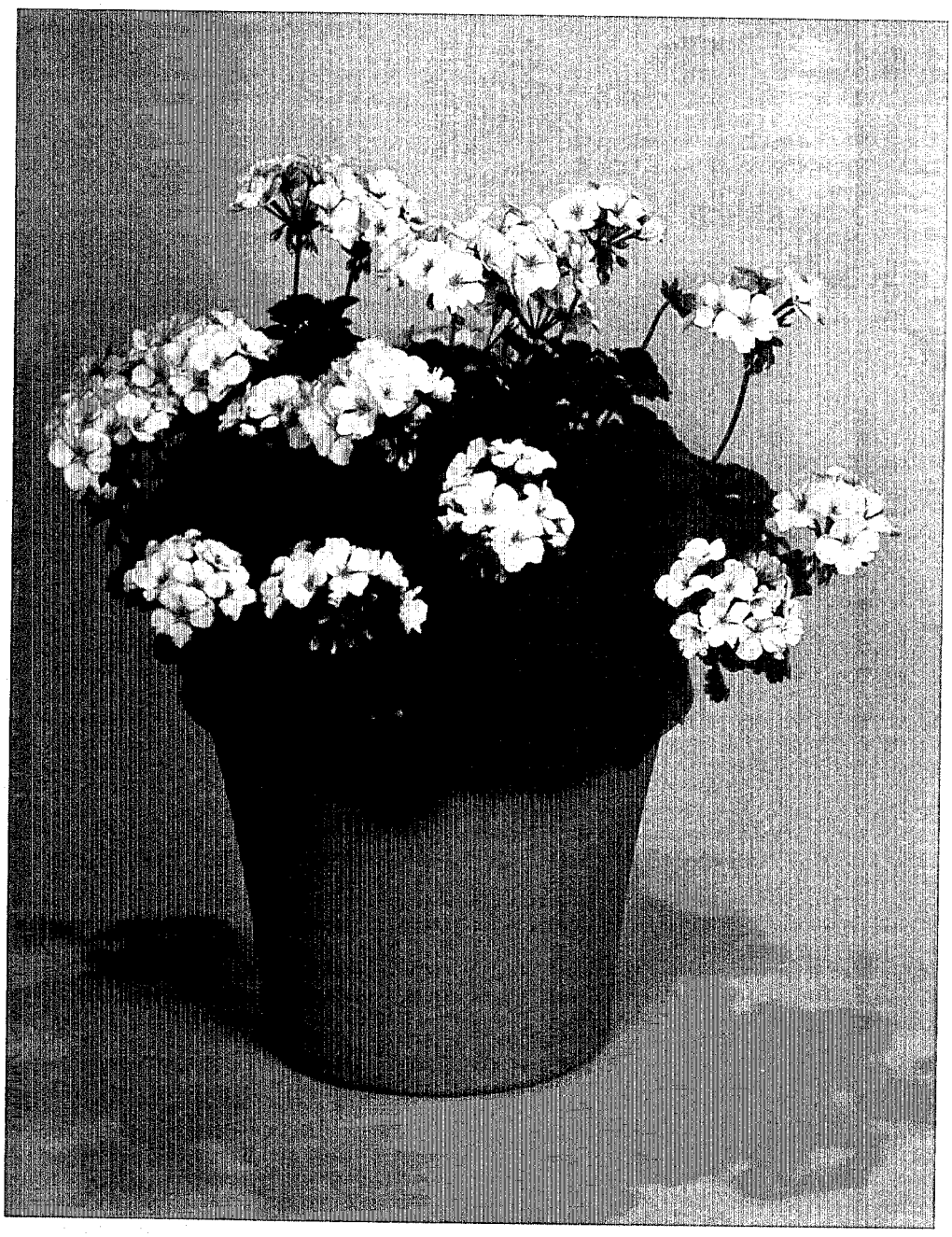

* * * * *